US010842722B2

(12) United States Patent
Moon et al.

(10) Patent No.: US 10,842,722 B2
(45) Date of Patent: Nov. 24, 2020

(54) PUMP-TYPE TOOTHPASTE COMPOSITION

(71) Applicant: LG Household & Health Care Ltd., Seoul (KR)

(72) Inventors: Kyo-Tae Moon, Daejeon (KR); Ji-Hye Lee, Daejeon (KR); Seong-Lok Hwang, Daejeon (KR); Won-Ho Ha, Daejeon (KR); Aram You, Daejeon (KR)

(73) Assignee: LG Household & Health Care Ltd. (KR)

( * ) Notice: Subject to any disclaimer, the term of this patent is extended or adjusted under 35 U.S.C. 154(b) by 0 days.

(21) Appl. No.: 16/479,080

(22) PCT Filed: Jan. 10, 2018

(86) PCT No.: PCT/KR2018/000485
§ 371 (c)(1),
(2) Date: Jul. 18, 2019

(87) PCT Pub. No.: WO2018/135797
PCT Pub. Date: Jul. 26, 2018

(65) Prior Publication Data
US 2019/0380928 A1 Dec. 19, 2019

(30) Foreign Application Priority Data

| Jan. 23, 2017 | (KR) | 10-2017-0010574 |
| Jan. 23, 2017 | (KR) | 10-2017-0010589 |
| Feb. 28, 2017 | (KR) | 10-2017-0026651 |
| Feb. 28, 2017 | (KR) | 10-2017-0026686 |

(51) Int. Cl.
*A61K 8/21* (2006.01)
*A61K 8/25* (2006.01)
*A61K 8/34* (2006.01)
*A61K 8/46* (2006.01)
*A61K 8/49* (2006.01)
*A61K 8/73* (2006.01)
*A61K 8/81* (2006.01)
*A61Q 11/00* (2006.01)

(52) U.S. Cl.
CPC .............. *A61K 8/21* (2013.01); *A61K 8/25* (2013.01); *A61K 8/345* (2013.01); *A61K 8/463* (2013.01); *A61K 8/49* (2013.01); *A61K 8/498* (2013.01); *A61K 8/73* (2013.01); *A61K 8/731* (2013.01); *A61K 8/8152* (2013.01); *A61K 8/8176* (2013.01); *A61Q 11/00* (2013.01)

(58) Field of Classification Search
CPC .................................. A61K 8/25; A47K 5/18
USPC .................................................. 424/49, 401
See application file for complete search history.

(56) References Cited

U.S. PATENT DOCUMENTS

| 2,792,856 | A | * | 5/1957 | Coppage ................. A47K 5/18 141/362 |
| 4,029,760 | A | * | 6/1977 | De Roeck born Holtzhauer ........ A61K 8/73 424/48 |
| 4,927,636 | A | * | 5/1990 | Hijiya ..................... A61K 8/73 424/409 |
| 5,120,528 | A | * | 6/1992 | Chang .................... A61K 8/466 424/49 |
| 5,628,985 | A | * | 5/1997 | Stiller ..................... A61K 8/25 424/49 |
| 2012/0020897 | A1 | | 1/2012 | Campbell et al. |
| 2012/0244203 | A1 | * | 9/2012 | Sakamoto ............... A61K 8/25 424/401 |
| 2015/0238395 | A1 | | 8/2015 | Plata et al. |
| 2016/0151255 | A1 | | 6/2016 | You et al. |

FOREIGN PATENT DOCUMENTS

| JP | H 07-126131 A | 5/1995 |
| JP | H 10-087457 A | 4/1998 |
| JP | 2001031542 A | 2/2001 |
| JP | 2008088144 A | 4/2008 |
| KR | 20110053021 A | 5/2011 |
| KR | 2014-0146985 A | 12/2014 |
| KR | 20160029433 A | 3/2016 |

(Continued)

OTHER PUBLICATIONS

International Search Report From PCT/KR2018/000485 dated May 8, 2018.

(Continued)

*Primary Examiner* — Walter E Webb
(74) *Attorney, Agent, or Firm* — Lerner, David, Littenberg, Krumholz & Mentlik, LLP

(57) ABSTRACT

The present disclosure relates to a pump-type toothpaste composition capable of being provided as contained in a pumping type container, and to a pump-type toothpaste composition improving the spreading property to a tooth as the toothpaste composition discharged to a toothbrush penetrates into the toothbrush and having an effect of ultimately delivering a medicinal ingredient continuously for a long time in the oral cavity.

In addition, the present disclosure relates to a pump-type toothpaste composition with excellent commercial value, which can ensure discharge stability without hardening and accordingly, can be used in a pump-type container equipped with a dispenser pump (dip pump), which has a remarkable problem of hardening in the discharge port due to free movement of external air because of properties of the container, and thus can ensure even the convenient use.

9 Claims, 1 Drawing Sheet

(56) References Cited

FOREIGN PATENT DOCUMENTS

KR    20160131488 A    11/2016
WO    2008-042279 A2    4/2008

OTHER PUBLICATIONS

Database GNPD [Online], Aug. 11, 2014 (Aug. 11, 2014), "Pumping Gel Style Toothpaste with Herb Flavour" XP055730803, retrieved from www.gnpd.com Database accession No. 2591569 * the whole document *.
Database GNPD [Online], Sep. 22, 2016 (Sep. 22, 2016), "Cool Mint Toothpaste", XP055730807, retrieved from www.gnpd.com Database accession No. 4297061 * the whole document *.
Extended European Search Report with Written Opinion for Application No. 18741570 dated Sep. 25, 2020, 7 pages.

* cited by examiner

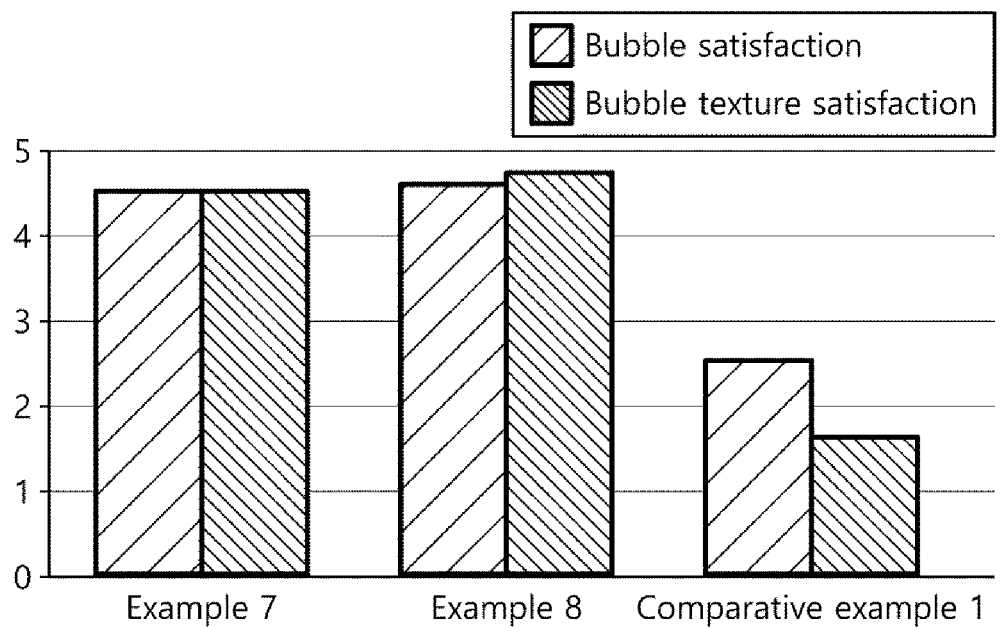

PUMP-TYPE TOOTHPASTE COMPOSITION

CROSS-REFERENCE TO RELATED APPLICATIONS

This application is a national phase entry under 35 U.S.C. § 371 of International Application No. PCT/KR2018/000485, filed Jan. 10, 2018, which claims priority to Korean Patent Application No. 10-2017-0010574, filed en-Jan. 23, 2017, Korean Patent Application No. 10-2017-0010589, filed Jan. 23, 2017, Korean Patent Application No. 10-2017-0026651, filed Feb. 28, 2017, and Korean Patent Application No. 10-2017-0026686, filed Feb. 28, 2017, the disclosures of which are incorporated herein by reference.

TECHNICAL FIELD

The present disclosure relates to a toothpaste composition to be provided as contained in a pump-type container.

More specifically, the present disclosure relates to a pump-type toothpaste in which the toothpaste composition penetrates into a toothbrush to improve a spreading property to a tooth and ensure discharge stability without hardening.

BACKGROUND ART

Toothpaste compositions commonly used for cleaning mouth and teeth include pastes, powders, gels/mucus or liquids, and their use and handling have certain advantages and disadvantages.

A paste type toothpaste originally developed in Colgate, USA, was sold in aluminum tubes and such aluminum tubes were still in use by the 1970s. The container of this paste type toothpaste has been developed as a laminated film material of aluminum as in modern times, and this is the development of polymer and polymer processing technology. However, this tube type of toothpaste has many inconveniences, for example, having problems of having high viscosity, being likely to cause damage to tooth enamel layers due to an abrasive ingredient, being inconvenient to squeeze during use as well as leaving residual toothpaste in a container to be discarded because products in the container cannot be used completely, and causing environmental pollution. In order to improve the releasability of such toothpaste and the like, a liquid toothpaste product having the flowing property in a plastic container has been developed, but when the it flows too well, it is difficult to effectively deliver a drug in the toothpaste product to teeth and gums. Accordingly, it has been widely used as an oral gargle that performs functions of inhibiting oral bacteria and removing bad breath, but it could not exhibit an effect of sufficient brushing such as removal of plaque in oral cavity and removal of oral bacteria and the like due to a problem of lack of cleaning ingredients and easy flow. There has been an attempt to apply a vacuum pump-type of plastic container to discharge high viscosity of paste, which has been applied next in order to enhance the user convenience of consumers, and some products are on the market, but they have price problems and poor releasability of conventional paste toothpastes and the like. In addition, powders are inconvenient in use since their particles are sprayed or scattered during its use. Moreover, in case of general high-viscosity paste type toothpaste or conventional liquid toothpaste, it is impossible to apply to various types of containers.

In addition, such common high-viscosity paste type toothpaste or conventional liquid toothpaste cannot be applied to various types of containers. In case of the high-viscosity paste type toothpaste, it is difficult to discharge when applying a dip tube type of pump, and discharge is impossible as the viscosity is further increased over time, and in case of the conventional liquid toothpaste, its use is impossible as it cannot maintain its shape on a toothbrush even if discharged. Furthermore, the moss hardness of an abrasive contained in toothpaste has a value of about 3-6, and thus it is higher than the hardness of the low-density polyethylene which is a piston of a dispenser pump. Thus, there is a problem that the piston wears due to the abrasive contained in the toothpaste and therefore the discharge is difficult.

DISCLOUSRE

Technical Problem

Accordingly, a problem to be solved by the present disclosure is to solve the aforementioned problem and provide a pump-type toothpaste composition which can be provided as contained in a pump-type container.

In addition, it is to provide a pump-type toothpaste composition in which the toothpaste composition discharged to a toothbrush penetrates into the toothbrush to improve the spreading property to a tooth.

Furthermore, it is to provide a pump-type toothpaste composition with ensured discharge stability without hardening.

Moreover, it is to provide a pump-type toothpaste composition which uses a dispenser pump (or 'dip pump) to have the convenient usability and is capable of being used without pump failure due to piston wear by abrasion and content hardening.

Technical Solution

To solve the aforementioned problems, one aspect of the present disclosure is to provide a pump-type toothpaste composition capable of being provided as contained in a pump-type container. More specifically, the present disclosure provides a pump-type toothpaste in which the toothpaste composition discharged to a toothbrush penetrates into the toothbrush to improve the spreading property to a tooth.

Hereinafter, it will be described in more detail.

For toothpaste discharged to a toothbrush and used, it is important to prepare it to penetrate into the toothbrush and deliver a medicinal ingredient continuously to a tooth during brushing. Therefore, it is required to solve disadvantages that the toothpaste flows on the toothpaste, when the flowability is too strong, and the toothpaste with high viscosity or high elastic modulus has a weak releasability and is completely exhausted when it reaches a tooth. In addition, it is important to prepare a toothpaste composition which penetrates into a toothbrush and at the same time, provides a feeling of bubbling to feel a rich feeling when brushing, but there is a difficulty in preparation of such a toothpaste composition.

Accordingly, the present inventors have found that a pump-type toothpaste composition penetrates into toothbrush bristles well and has a significant effect in improvement of spreading property to a tooth, and thereby it has an excellent effect of delivering a medicinal ingredient continuously to a tooth for a long time and in addition, it has an effect of providing a rich feeling during brushing, by controlling the kind and/or content of binders used in the pump-type toothpaste composition contained in a pump-type container, and have completed the present invention.

More specifically, it has been confirmed that it is possible to improve the spreading property to a tooth and provide rich feeling of brushing, when comprising a binder of which content is 0.1% by weight or more to less than 2.5% by weight based on the total weight of the composition, or using one or more kinds selected from the group consisting of PVM/MA, PVP, HPMC, and HPC as a binder, in the pump-type toothpaste composition.

In the specification according to the present invention, the term 'pumping type' means a structure capable of releasing contents stored inside of a container to the outside through a discharge port by pump action using a pushing member of the container. Specifically, it means a structure of releasing a toothpaste composition inside of a container to the outside of the container through pump action of a piston to use, and in other words, by the pump action, contents can be released from the inner bottom of the container to the outside by a piston equipped inside of the container.

The present disclosure provides a pump-type toothpaste composition comprising a specific content range and/or a specific kind of binder.

The 'binder' means an ingredient that allows toothpaste to remain in a stable and uniform form, and it may include various ingredients commonly available as a binder in a toothpaste composition commonly in the art. For example, it includes sodium carboxymethyl cellulose, copolymer of methyl vinyl ether and maleic anhydride (PVM/MA), poly vinyl pyrrolidone (PVP), hydroxy propyl methyl cellulose (HPMC), hydroxy methyl cellulose (HMC), hydroxy propyl cellulose (HPC), carbomer, carrageenan, xanthan gum, guar gum, polyacrylic acid/sodium and alginates and the like, but not limited thereto. It is interpreted that an ingredient that exhibiting other functions in addition to the function as a binder is included in the binder defined in the present disclosure and is not excluded.

The pump-type toothpaste composition according to the present disclosure is provided in a gel form.

In the specification according to the present invention, the term 'gel' is used as a concept to distinguish between conventional liquid toothpaste in a dilute form and a high viscosity of paste toothpaste. The gel is a formulation to be distinguished from the conventional liquid formulation, and means a formulation having a greater degree of stickiness than the liquid toothpaste and is viscous. The toothpaste in a gel form of the present disclosure means a formulation having elasticity and rigidity than the liquid toothpaste. In addition, the gel toothpaste of the present disclosure has fluidity due to lower viscosity than a paste type of toothpaste and can easily discharge contents to the outside due to flowability.

In the specification according to the present invention, the term 'elasticity' means a property that an object deformed by an external force tries to return to its original shape when the force is removed, and it has been used as a broad concept meaning a property of an object that is intended to maintain its original form. In other words, it has been used as a broad meaning including all properties to intend to maintain the original shape after discharging a toothpaste composition from a discharge port.

As one aspect, the present disclosure provides a pump-type toothpaste composition, characterized by comprising one or more binders selected from the group consisting of copolymer of methyl vinyl ether and maleic anhydride (PVM/MA), poly vinyl pyrrolidone (PVP), hydroxy propyl methyl cellulose (HPMC), and hydroxy propyl cellulose (HPC) (hereinafter, refer to 4 kinds).

Herein, when using one or more of the 4 kinds as a binder, in addition to these binders, selectively, other binders known in the art as a binder can be additionally used. Other binders include sodium carboxy methyl cellulose, carbomer, carrageenan, xanthan gum, guar gum, polyacrylic acid/sodium and alginates and the like, but not limited thereto.

The total content of one or more binders of the 4 kinds may be 0.1-7% by weight, more preferably 0.3-5% by weight, much more preferably 0.5-2.5% by weight, based on the total weight of the pump-type toothpaste composition. When using a binder in the aforementioned range, a toothpaste composition having appropriate viscosity can be prepared, and it has an effect capable of preparing a toothpaste composition which easily penetrates into gaps of toothbrush bristles.

The total content of binders comprised in the toothpaste composition according to the present disclosure including one or more binders of the 4 kinds may be 0.5-8% by weight, more preferably 0.5-6% by weight, much more preferably 0.5-5% by weight, based on the total weight of the pump-type toothpaste composition. When using a binder in the aforementioned range, a toothpaste composition having appropriate viscosity can be prepared, and it has an effect capable of preparing a toothpaste composition which easily penetrates into gaps of toothbrush bristles.

The pump-type toothpaste composition comprising one or more binders of the 4 kinds according to the present disclosure penetrates into bristles gaps within 10 seconds when discharging it to a toothbrush having an interval of toothbrush bristles of 1-1.5 mm. More specifically, it penetrates in a depth of 5 nm or less. The term 'depth' means a length at which toothpaste extends from the top of the bristles to the bottom.

The pump-type toothpaste composition comprising one or more binders of the 4 kinds according to the present disclosure has the viscosity of $5 \times 10^3$ cP or more to $60 \times 10^3$ cP or less at a room temperature (25□). The viscosity may be measured by various methods known in the art, and for example, it may be measured by rotating at a rotation speed of 10 rotations per minute using spindle No. 7 with Brookfield viscometer RVT type, but not limited thereto.

The pump-type toothpaste composition comprising one or more binders of the 4 kinds according to the present disclosure has Tan δ (Loss modulus (G")/Elastic Modulus (G') of 0.4 or more. The present disclosure provides a toothpaste composition with excellent rich feeling, by using the 4 kinds that are polymers having a high viscosity coefficient and at the same time having excellent flowability.

The pump-type toothpaste composition comprising one or more binders of the 4 kinds according to the present disclosure exhibits excellent rich feeling.

In the specification according to the present invention, the term 'rich feeling' refers to sensation of the mouth due to texture and viscosity of bubbles that occur when brushing.

As another aspect, the present disclosure provides a pump-type toothpaste composition contained in a pump-type container, characterized in that the content of a binder is 0.5% by weight or more based on the total weight of the composition. More specifically, it is less than 2.5% by weight based on the total weight of the composition. Much more specifically, it is 1.5% by weight or less based on the total weight of the composition. When it is 2.5% by weight or more based on the total weight of the composition, a toothpaste composition which does not penetrates into bristles and is highly viscous is prepared.

As the binder, a binder known in the art as a binder of a toothpaste composition may be used, and for example, one or more kinds of sodium carboxymethyl cellulose, copolymer of methyl vinyl ether and maleic anhydride (PVM/MA), poly vinyl pyrrolidone (PVP), hydroxy propyl methyl cellulose (HPMC), hydroxy methyl cellulose (HMC), hydroxy propyl cellulose (HPC), carbomer, carrageenan, xanthan gum, guar gum, polyacrylic acid/sodium and alginates and the like may be used.

The pump-type toothpaste composition comprising a binder of 0.5% by weight or more based on the total weight of the composition according to the present disclosure penetrates into bristles gaps in a depth of 1 mm or more within 10 seconds, when discharging it to a toothbrush having an interval between bristles of 1.5 mm. In addition, when discharging it to a toothbrush having an interval between bristles of 2 mm, it penetrates into the spaces of bristles in a depth of 1.5 or more within 10 seconds. The term 'depth' means a length at which toothpaste extends from the top of the bristles to the bottom.

The pump-type toothpaste composition comprising a binder of 0.5% by weight of more based on the total weight of the composition according to the present disclosure has viscosity of $5 \times 10^3$ cP or more to $40 \times 10^3$ cP or leas at a room temperature (25□). The viscosity may be measured by various methods known in the art, and for example, it may be measured by rotating at a rotation speed of 20 rotations per minute using spindle No. 7 with Brookfield viscometer RVT type, but not limited thereto.

The toothpaste composition according to the present disclosure may further comprise a flavoring agent, a sweetening agent, a pharmaceutical agent, a pH adjusting agent, a preservative, a binder, a foaming agent, a whitening agent, and the like, depending on its implementation and use purpose, as an ingredient commonly used in the art as a tooth paste composition.

Preferably, the toothpaste composition according to the present disclosure is provides as a pump-type toothpaste composition, and therefore it is preferable to comprise a small amount of abrasive for prevention of pump wear, and it is preferable to comprise a lubricant (polyol, glycerin, and the like) to prevent clogging of the discharge port by drying.

The abrasive is a material having a function to remove dental plaque (plaque) in the oral cavity, and is necessarily used to enhance the efficiency of removal of plaque and remove hard foreign substances and the like, and it shows a value of Mohs hardness of about 1-6. Herein, a piston of a pump container is prepared with low-density polyethylene, and it is preferable to comprise an abrasive in a small amount, since the pump may wear as the hardness of the polyethylene is lower than the hardness of the used abrasive. For example, it may be comprised in an amount of 30% by weight or less, preferably 0.5 to 20% by weight, based on the total weight of the composition. The abrasive may include for example, any one selected from the group consisting of calcium hydrogen phosphate, precipitated silica, fumed silica, colloidal silica, zeolite, calcium carbonate, hydrated alumina, kaolin, cellulose and mixtures thereof, but not limited thereto.

The lubricant means a substance which acts to reduce friction between two surfaces that are in contact each other and slide, and the lubricant plays a role of prevent wear of a piston by raw materials (solids such as abrasive) showing a wear property contained in the toothpaste composition of the present disclosure by lubrication action. For example, the lubricant may include any one selected from the group consisting of polyethylene glycol, glycerol, propylene glycol, ethylene glycol, polypropylene glycol and mixtures thereof, but not limited thereto. Preferably, it may comprise any one selected from the group consisting of polyethylene glycol 200 to 600, glycerol, propylene glycol, ethylene glycol, polypropylene glycol and mixtures thereof. Preferably, as a liquid lubricant, petroleum-based oil, animal and vegetable oil, synthetic lubricant oil and the like may be used, and most preferably, liquid polyol may be used in terms of stability and excellent sensation of use of the composition. Otherwise, the lubricant is not limited to the liquid polyol, but it includes high molecular weight of polyol which can be present in a solid phase at a room temperature in an amount of certain molecular weight by intramolecular interaction of polymers but can be liquefied through control of preparation temperature and can be manufactured and maintained in a stable state, such as polyethylene glycol and polypropylene glycol which have a polymer form.

In the composition of the present invention, a flavoring agent and a sweetening agent may be added to suit tastes of consumers. The flavoring agent remains in the oral cavity and emits fragrance continuously so that exhilaration continues.

As a flavoring agent, mint such as peppermint, spearmint, and the like, wintergreen, methyl salicylate, eugenol, melon, strawberry, orange, vanillin and the like may be used. In general, the flavoring agent may be used in a range of 0.001 to 10% by weight based on the total weight of the composition.

In addition, in the composition of the present invention, a sweetening agent may be added to overcome the basic taste of formulations. The sweetening agent can play a role of maintaining occurrence of saliva by remaining in the oral cavity and providing the taste continuously.

As a sweetening agent, 1 kind or 2 kinds of saccharine, sucralose, sugar, xylitol, sorbitol, lactose, mannitol, maltitol, erythritol, aspartame, taurine, saccharine salt, D-tryptophan and the like may be mixed to use. Among saccharine salts, sodium saccharine is most widely used. The amount of the sweetening agent is generally in the range of 0.001 to 20% by weight of the total weight of the composition.

As a pharmaceutical agent used for oral hygiene, ingredients having an effect of cavity prevention, gum disease prevention, tartar deposition prevention, whitening, and the like may be used. The pharmaceutical agent used on purpose of cavity prevention includes a compound approved as a safe substance by United States Food and Drug Administration. The compound used as a supply source of fluorine ion may include sodium fluoride, sodium monofluorophosphate, stannous fluoride, ammine fluoride. The content of fluorine may differ in usage depending on countries, but it is general to use a mixture of one kind or 2 kinds of these supply sources so as to have a concentration of fluorine ion in a range of preferably 850 to 1500 ppm. A recalcification agent also may act as a cavity preventing agent. Recalcification plays a role of regenerating and restoring a major constituent of teeth, hydroxyapatite. The major component of hydroxyapatite consists of divalent calcium cation and phosphate anion. Thus, one which supplies calcium ion and phosphate ion at the same time or includes one or more kinds of calcium divalent ion or phosphate anion, so that the chemical equilibrium in the oral cavity moves to the side at which hydroxyapatite is produced may be used as the recalcification agent. The material providing calcium and phosphate includes hydroxyapatite in raw material, dibasic calcium phosphate, calcium chloride, casein, phosphopeptide, calcium glycerophosphate, monobasic sodium phosphate, dibasic sodium phosphate, tribasic sodium phosphate, monobasic potassium phosphate, dibasic potassium phosphate, tribasic potassium phosphate and the like. In general, it is preferable to use the recalcification agent in a range of 0.001 to 20% by weight of the total composition. When it is less than 0.001% by weight, the recalcification effect is reduced, and when it is more than 20% by weight, a property which a formulation originally has may be lost. One of purposes of using an oral hygiene item is to alleviate a proceeding gum disease, as well as to prevent a gum disease in advance, by sterilization or anti-inflammation action against harmful microorganisms in the oral cavity. For this purpose, isopropyl methyl phenol, cyclohexidine, cetyl pyridinium chloride, xanthorrhizol and the like known as antibacterial agents may be used, and for anti-inflammation action, vitamins and enzyme, aminocaproic acid, allantoin and derivatives thereof and the like may be used. The pharmaceutical agent may be contained in an amount of 0.005% by weight to 5% by weight. When the content of pharmaceutical agent is less than 0.005, it is difficult to exhibit a medicinal effect, and when it is contained in an amount over 5% by weight, there is a disadvantage of changing the taste of fundamental base. Hydrogen peroxide, carbamide peroxide, calcium peroxide, and the like showing a whitening effect in addition to gum diseases may be used, and to obtain an effect of inhibiting plaque deposition, sodium pyrophosphate, acidic sodium pyrophosphate, potassium pyrophosphate, sodium metaphosphate, and the like are also used. In general, these pharmaceutical agents are used in a range of 0.001 to 10% by weight of the total weight of the composition.

As a pH adjusting agent, phosphate, sodium phosphate, citric acid, sodium citrate, succinic acid, sodium succinate, tartaric acid, sodium tartrate, and the like may be used, and the acidity of an oral composition is generally 5 to 8.

As a preservative, benzoic acid, methyl paraben, propyl paraben, sodium benzoate, and the like may be used.

As a bubbling agent, one or 2 kinds or more of anion, amphoteric, and non-ionic surfactants such as sodium alkyl sulfate, sodium lauryl sulfate, alkyl sarcosinate, lauryl sarcosinate, sodium cocoyl glutamate salt, sodium myristoyl glutamate salt, cocamidopropyl betaine, sucrose fatty acid ester, sorbitan fatty acid ester, polyoxyethylene-polyoxypropylene block copolymer (poloxamer) may be mixed to use.

As a whitening agent, titanium oxide is used, and generally, it is used in an amount of 0.1% to 2% by weight.

A method for preparing the toothpaste of the present disclosure may prepare it according to the common method for preparing in the art.

The toothpaste composition of the present disclosure may be converted into mouthwash, cleansing agent for an artificial tooth, and the like.

Other aspect of the present disclosure is to provide a pump-type toothpaste composition which can be provided as contained in a pump-type container. More specifically, the present disclosure provides a pump-type composition which can be provided as contained in a pump-type container equipped with a dispenser pump (or refer to 'dip pump').

The pump-type toothpaste composition is discharged through a pump of a pump-type container, but all phases of solid, liquid and gas are present in the discharge port, and therefore the toothpaste composition contact with them is hardened in the inlet of discharge port, which has been a problem. Moreover, an abrasive is generally comprised in a toothpaste composition to remove dental plaque and the like, but when the toothpaste composition is prepared as a pumping type, there is a problem of occurring wear of a piston due to hardness of the abrasive. The piston is prepared with low-density polyethylene, and such a problem becomes more serious when the hardness of the polyethylene is lower that the hardness of the abrasive.

Accordingly, the present inventors have found that the pump-type toothpaste composition has an effect of securing the discharge stability without hardening in the discharge port, by controlling kinds and/or contents of ingredients used for the pump-type toothpaste composition contained in a pump-type container, thereby completing the present invention.

More specifically, as one aspect, it has been confirmed that the pump-type toothpaste composition has an effect of securing the discharge stability without hardening in the discharge port, when the content of the solid abrasive is 40% by weight or less based on the total weight of the composition and the content of water is less than 7% by weight based on the total weight of the composition, in the pump-type toothpaste composition.

As other aspect, it has been confirmed that the pump-type toothpaste composition has an effect of securing the discharge stability without hardening in the discharge port, when it comprises a non-ionic surfactant having an HLB value of 16 or less, in the pump-type toothpaste composition.

The HLB value of the non-ionic surfactant may be 16 or less, preferably 10 or less, more preferably 8 or less, much more preferably 6 or less.

As other aspect, it has been confirmed that the pump-type toothpaste composition has an effect of securing the discharge stability without hardening in the discharge port, when it comprises organic oil having a specific gravity of 0.8-0.99, in the pump-type toothpaste composition.

By pump action, the contents to be discharged to the outside by the piston equipped inside of the container contact with a solid, liquid or gas phase present in the pump discharge port, during releasing (discharging) or after releasing (discharging).

Herein, as the pump used in the pump-type container, for example, a dispenser pump (dip pump), an e-sensor pump, an oil pump, a foaming pump, a mist pump and the like may be used, and preferably, a dispenser pump (dip pump) may be used.

The 'dispenser pump (dip pump)' is convenient to use due to soft feeling during pumping, accurate and various discharge amounts, and viscosity of contents, and it is commonly used for shampoo or bodywash products. The 'E-sensor pump' has an advantage capable of making the discharge amount small and fine. The 'oil pump' is an effective pump in case of supporting contents in which fluid leakage may be caused when used. The 'foaming pump' is a pump having an advantage capable of making rich foam by the internal structure of the pump without using Freon gas. The 'mist pump' is a pump having a structure of spraying contents in a fine particle form.

The present disclosure provides a pump-type toothpaste composition contained in a pump-type container, comprising specific ingredients and/or their specific content ranges.

The pump-type toothpaste composition according to the present disclosure is not hardened in a pump discharge port, and thus it exhibits the discharge stability.

More specifically, any one or more of pump-type toothpaste compositions of the toothpaste composition of one aspect, the toothpaste composition of another aspect, and the toothpaste composition of other aspect as described below are not hardened in a pump discharge port and exhibit the discharge stability.

In the specification of the present invention, the term 'harden' means the increase of hardness or hardness scale of the toothpaste composition, and it means that the scale of resistance to modification of the toothpaste composition increases when applying pressure to the toothpaste composition using other object. By various methods known in the art, 'hardness' may be measured or evaluated, and it is not limited to methods as described below, for example, a method for evaluating a degree of hardening when applying pressure using a probe-rod (round-shaped pen), or a method for measuring the compression strength with a 0.4~2 cm probe using a texture analyzer, and the like may be used. Otherwise, a method for measuring the pump pressure of a pump after discharging a toothpaste composition using a texture analyzer may be used.

In the specification of the present invention, the term 'not harden' means no or little increase of hardness or hardness scale of the toothpaste composition, and for example, by the method for evaluating the degree of hardening when applying pressure using a probe-rod (round-shaped pen), it is evaluated as 'not harden' that a toothpaste composition is scratched or the probe-rod is inserted into contents when drying the toothpaste composition discharged at 60□ for 48 hours and then applying pressure. In addition, for example, by the method for measuring the compression strength with a 0.4~2 cm probe using a texture analyzer, it is evaluated as 'not harden' that the compression strength measured after drying the discharged toothpaste composition at 60□ for 48 hours is shown as 5 g or less. Furthermore, for example, by the method for measuring the pump pressure of a pump after discharging a toothpaste composition using a texture analyzer, it is evaluated as 'not harden' that the discharge pressure of 3 kg or less is shown when measuring the pump pressure using a texture analyzer after discharging a toothpaste composition and then drying it at 60□ for 6 hours.

Any one or more of pump-type toothpaste compositions of the toothpaste composition of one aspect, the toothpaste composition of another aspect, and the toothpaste composition of other aspect as described below are not hardened in a pump discharge port, and therefore, for example, by the method for evaluating the degree of hardening when applying pressure using a probe-rod (round-shaped pen), the toothpaste composition is scratched or the probe-rod is inserted into contents when applying pressure after drying the discharged toothpaste composition at 60□ for 48 hours. In addition, by the method for measuring the compression strength with a 0.4~2 cm probe using a texture analyzer, the compression strength measured after drying the discharged toothpaste composition at 60□ for 48 hours is shown as 5 g or less. Furthermore, by the method for measuring the pump pressure of a pump after discharging a toothpaste composition using a texture analyzer, the discharge pressure of 3 kg or less is shown when measuring the pump pressure using a textures analyzer after discharging a toothpaste composition and then drying it at 60□ for 6 hours.

In the specification of the present invention, the term 'discharge stability' means an effect shown in case that the toothpaste composition is 'not hardened'.

The toothpaste composition according to the present disclosure is not hardened due to viscosity change or the like.

Preferably, any one or more of pump-type toothpaste compositions of the toothpaste composition of one aspect, the toothpaste composition of another aspect, and the toothpaste composition of other aspect may have a viscosity of 5,000 cP to 30,000 cP.

In the specification of the present invention, the term 'viscosity' means the viscosity size of the toothpaste composition, and 'viscosity retentivity' means the degree of maintaining the viscosity of toothpaste when prepared constant at least 2 years. Preferably, the viscosity retentivity means that the viscosity change of the composition is about 100 to 15,000 cP after at least 2 years as compared to the time of preparation, when measuring the viscosity with BrookField, RVT type No. 7 spindle or RV-5, under the conditions of 25□, 20 rpm, and 5 cycle.

As one aspect, the present disclosure provides a pump-type toothpaste composition contained in a pump-type container, in which the content of solid abrasive is 40% by weight or less based on the total weight of the composition and the content of water is less than 7% by weight based on the total weight of the composition.

The present inventors have confirmed that the reason why the toothpaste composition is dried is because the solid content, particularly, the solid abrasive, in contents is expressed as the water contained in the composition evaporates, and by increasing the content ratio of water to the solid abrasive, in order to solve this problem, have materialized the present invention.

The 'abrasive' is a material functioning to remove dental plaque (plaque) in the oral cavity, and it is commonly used in a toothpaste composition to enhance the efficiency of removal of dental plaque and remove hard foreign substances and the like, but it wears out a pump and hardens a pump discharge port. The abrasive may show a value of about 1~6 Mohs hardness, preferably, about 3~6 Mohs hardness.

Herein, the solid abrasive may include all which is used as a solid abrasive of a toothpaste composition in the art, and for example, calcium monohydrogen phosphate, precipitated silica, fumed silica, colloidal silica, zeolite, calcium carbonate, calcium hydrogen phosphate, hydrated alumina, kaolin, cellulose and mixtures thereof and the like are included, but not limited thereto. Preferably, precipitated silica, calcium carbonate, calcium hydrogen phosphate or mixtures of two or more thereof may be used.

Herein, the content of the solid abrasive may be 40% by weight or less based on the total weight of the composition, and for example, it may be 30% by weight or less, 20% by weight or less, 10% by weight or less, or 5% by weight or less. For example, it may be 0.1% by weight or more, and it may be 0.1% by weight or more to 40% by weight or less, 0.5% by weight or more to 40% by weight or less, or 0.5% by weight or more to 20% by weight or less. When it is over 40% by weight, hardening of the toothpaste composition in a discharge port is caused.

Herein, the 'water' is a material playing a role as a solvent of ingredients comprised in the toothpaste composition, and the water includes for example, purified water purified by distilling top water or ion exchange resin, distilled water, sterile purified water, water for injection, top water and the like, and preferably, sterile purified water may be used.

Herein, the content of water may be less than 10% by weight, less than 7% by weight, or less than 6% by weight, based on the total weight. Otherwise, it may be 3% by weight or more to less than 10% by weight, or 5% by weight or more to less than 7% by weight. When it is over 10% by weight, hardening of the toothpaste composition in a discharge port is caused.

Herein, the content ratio of water based on the solid abrasive may be 1:0.1 or more, preferably 1:0.1-1. When it is less than 1:0.1, hardening of the toothpaste composition in a discharge port is caused.

The toothpaste composition according to the present disclosure may further comprise various ingredients according to its implementation and use purposes, as ingredients commonly used as a toothpaste composition in the art, in addition to the solid abrasive and water.

However, preferably, solid ingredients other than the solid abrasive are not substantially comprised in the toothpaste composition according to the present invention.

In the specification of the present invention, the term 'not substantially comprised' means a content of 1% by weight or less, 0.5% by weight or less, 0.1% by weight or less, preferably 0% by weight (namely, not comprised at all), based on the total weight of the composition.

As another aspect, the present disclosure provides a pump-type toothpaste composition contained in a pump-type container, comprising a non-ionic surfactant having an HLB value of 16 or less, preferably 10 or less, more preferably 8 or less, much more preferably 6 or less.

The present inventors have confirmed that when a non-ionic surfactant having an HLB value of 16 or less, the hydrophobic group of the surfactant is arranged to the outside when discharging a toothpaste composition and it becomes a suspended state in which a hydrophobic array is formed, and thus rising on the surface of water in contents is inhibited, thereby having an effect of solving a problem of hardening. In addition, it has been confirmed that the suspended state of the hydrophobic array formed by the non-ionic surfactant having an HLB value of 16 or less reduces wear of a piston when contacting with a polymer applied to a straw and a pump piston, and therefore there is an effect of facilitating the improvement of pumping stability, thereby materializing the present invention.

Herein, the term 'HLB' is an abbreviation of hydrophile-lipophile balance, and it is an index representing the balance of hydrophile and lipophile of a surfactant, and when HLB is large, it means the ratio of hydrophile is large and when HLB is small, it means the ratio of hydrophile is small.

Herein, as 'non-ionic surfactant having an HLB value of 16 or less', various ingredients to be comprised in a toothpaste composition in the art may be used, and it includes for example, glyceryl monostearate, polyoxyethylene monooleate (product name: PEG 400 monooleate), polyoxyethylene monostearate (product name: PEG 400 monostearate), potassium oleate, sodium oleate, sorbitan monolaurate (product name: Span® 20), sorbitan monopalmitate (product name: Span® 40), sorbitan monostearate (product name: Span® 60), sorbitan tristearate (product name: Span® 65), sorbitan monooleate (product name: Span® 80), sorbitan trioleate (product name: Span® 85), triethanolamine oleate, polyoxyethylene sorbitan monolaurate (product name: Tween® 21), polyoxyethylene sorbitan monopalmitate (product name: Tween® 40), polyoxyethylene sorbitan monostearate (product name: Tween® 60, Tween® 61), polyoxyethylene sorbitan tristearate (product name: Tween® 65), polyoxyethylene sorbitan monooleate (product name: Tween® 80, Tween® 81), polyoxyethylene sorbitan trioleate (product name: Tween® 85) or mixtures of two or more thereof, but not limited thereto.

Herein, the content of the non-ionic surfactant having an HLB value of 16 or less is 0.1-10% by weight, more preferably 0.1-5% by weight based on the total weight of the composition. In the weight range, hardening of the toothpaste composition can be inhibited and it is possible to facilitate to improve the pumping stability by inhibiting the wear of a piston.

As other aspect, the present disclosure provides a pump-type toothpaste composition contained in a pump-type container, comprising organic oil having a specific gravity of 0.8-0.99.

The present inventors have materialized the preset invention, based on that a pump-type composition used as contained in a pump-type container, particularly, a pump-type container equipped with a dip pump among toothpaste compositions commonly uses technology of increasing the composition of liquids to prevent drying, but rather, it becomes a reason causing hardening of a pump discharge port as water and volatile organic substances contained in contents are vaporized.

Accordingly, they have confirmed that when containing oil having a specific gravity of 0.8-0.99 in a pump-type toothpaste composition, the hydrophobic oil is arranged toward the air in a pump discharge port and inhibits evaporation of water in the pump-type toothpaste composition, to solve hardening of the discharge port.

Moreover, it has been confirmed that oil has an effect of extending the lifespan of a pump by minimizing the damage of a pump to be caused by friction with an abrasive, as it can reduce the frictional force by an abrasive, thereby completing the present invention.

Herein, the term 'specific gravity' means the ratio of the weight to the volume, and it means the ratio of the mass of a substance holding a certain volume at a certain temperature and the mass of a standard substance holding the same volume at the same temperature. The unit of specific gravity is $g/cm^3$.

Herein, '0.8-0.99 specific gravity' means that the ratio of the mass of organic oil holding a volume at 20-25□ and the mass of purified water holding the same volume at the same temperature is 0.8-0.99. Here, when a substance having a specific gravity of over 0.99, a problem of sinking to the lower part of the formulation may be caused, and when oil having a specific gravity of less than 0.8, the stability of the formulation may be lowered by ease volatilization.

Herein, as the oil having a specific gravity of 0.8-0.99, any one used as an ingredient of a toothpaste composition in the art may be used without limitations, and for example, it includes for example, coconut oil, cottonseed oil, olive oil, sunflower oil, rice kernel oil, corn oil, palm oil, palm kernel oil, peanut oil, safflower oil, castor oil, canola oil, grape seed oil, avocado oil, walnut oil, clove oil, peppermint oil, spearmint oil, vanillin oil, anise, anethole oil and the like, but not limited thereto. The coconut oil is 0.925 at 15□, and 0.919 at 20□, and the cottonseed oil is 0.926 at 16□ and 0.915-0.921 at 25□, and the olive oil is 0.918 at 15□ and 0.915-0.918 at 15.5□. Preferably, the oil may be organic oil, and preferably, the oil may be liquid oil which is liquid at a room temperature.

Preferably, herein, the content of the oil having a specific gravity of 0.8-0.99 is 0.3% by weight or more, more specifically, 0.3-20% by weight, based on the total weight of the composition. Most specifically, it is 0.3-10% by weight. In the % by weight range, it is effective in solving hardening of the toothpaste composition.

Preferably, the toothpaste composition according to the present disclosure may further comprise an emulsifier in addition to the oil having a specific gravity of 0.8-0.99, and it is preferable to particularly use sodium lauryl sulfate (SLS) among emulsifiers. According to a specific example, it has been confirmed that sodium lauryl sulfate can not only facilitate oil emulsification of toothpaste as a surfactant but also provide feeling of bubbles to consumers, thereby effectively eliminating the slip after brushing which may occur by oil.

In the toothpaste composition according to the present invention, the emulsifier emulsifies the oil comprised in the toothpaste composition, and it solves hardening of the discharge port by inhibiting evaporation of water in the pump-type toothpaste composition as the oil other than the oil to be emulsified is oriented toward the air. Then, when sodium lauryl sulfate (SLS) is selected as the emulsifier, it is characterized in that the oil other than the oil to be emulsified among oil comprised in the toothpaste composition can be oriented toward the air.

Herein, the total weight of the surfactant comprised in the composition based on the total weight of the oil having a specific gravity of 0.8-0.99 is 0.1-7% by weight, preferably 0.5-3% by weight. When it is less than 0.1% by weight, it is impossible to solve hardening of the toothpaste composition and it is impossible to remove the slip of teeth after use, and when it is over 7% by weight, there is a problem which may damage the oral mucosa during brushing.

Herein, any one or more of pump-type toothpaste compositions of the toothpaste composition of one aspect, the toothpaste composition of another aspect and the toothpaste composition of other aspect as described above may further comprise an abrasive, a lubricant, a flavoring agent, a sweetening agent, a pharmaceutical agent, a pH adjusting agent, a preservative, a binder, a foaming agent, a whitening agent and the like, as ingredients commonly used in the art as a toothpaste composition, depending on its formulation and use purpose, in addition to the ingredients comprised necessarily.

The following each ingredient and content range described regarding them are commonly used ingredients and content %, and therefore those skilled in the art can adjust them appropriately depending on its formulation and use purpose.

In addition, if there is a description that is inconsistent with the ingredients and content range thereof described in any one or more of pump-type toothpaste compositions of the toothpaste composition of one aspect, the toothpaste composition of another aspect and the toothpaste composition of other aspect as described above, it is preferable to use the above description as a reference.

The present disclosure provides pump-type toothpaste comprising any one or more of pump-type toothpaste compositions of the toothpaste composition of one aspect, the toothpaste composition of another aspect, and the toothpaste composition of other aspect, as described above, and a pump-type container in which the pump-type toothpaste composition is supported.

The pump-type toothpaste according to the present disclosure is not hardened, and for example, it may exhibit a discharge pressure of 3 kg or less, when measuring the pump pressure using a texture analyzer after discharging toothpaste and then drying at 60□ for 6 hours.

Advantageous Effects

According to the present disclosure, a pump-type toothpaste composition capable of being provided as contained in a pump-type container is provided, and in particular, the pump-type toothpaste composition has an effect of improving the spreading property to a tooth as the toothpaste composition discharged to a toothbrush penetrates into the toothbrush and ultimately delivering a medicinal ingredient continuously for a long time in the oral cavity.

In addition, the present disclosure can provide a pump-type toothpaste composition with excellent commercial value, which can ensure discharge stability without hardening and accordingly, can use a pump-type container equipped with a dispenser pump (dip pump) having a remarkable problem of discharge port hardening due to free movement of external air because of properties of the container, and thus can ensure even the convenient use.

BRIEF DECRIPTION OF THE DRAWINGS

The following drawings accompanied herein illustrate preferable examples of the present invention, and serve to further understand the technical idea of the present disclosure together with the aforementioned disclosure, and thus the present disclosure should not be construed as being limited to the matters described in such drawings.

The FIG. is a graph showing the values of evaluating the bubble satisfaction and bubble texture satisfaction of the compositions (Example 7, Example 8, and Comparative example 1) prepared according to Preparative example 2 of the following II. Pump-type toothpaste composition.

MODE FOR INVENTION

Hereinafter, the present disclosure will be described with reference to the following examples and the like to describe the present disclosure in more detail. However, the examples according to the present disclosure can be modified into various other forms, and the scope of the present disclosure should not be construed as being limited to the examples described below. The examples of the present disclosure are provided illustratively in order to facilitate a specific understanding of the present invention.

I. PREPARATIVE EXAMPLE 1 OF PUMP-TYPE TOOTHPASTE COMPOSITION

The toothpaste compositions of Examples and Comparative example were prepared with ingredients and composition ratios shown in the following Table 1. Powder ingredients such as purified water, liquid polyol, flavoring, a pharmaceutical agent, a surfactant, a binder, saccharine were completely dispersed to mix primarily, and then an abrasive such as silica and the like and a pharmaceutical agent were added and mixed in a vacuum to prepare toothpaste compositions.

TABLE 1

|  | Example 1 | Example 2 | Example 3 | Example 4 | Example 5 | Comparative example 1 |
|---|---|---|---|---|---|---|
| Precipitated silica | 15.00 | 15.00 | 15.00 | 15.00 | 15.00 | 15.00 |
| Glycerin | 50.00 | 50.00 | 50.00 | 50.00 | 50.00 | 50.00 |
| Sodium lauryl sulfate | 2.20 | 2.20 | 2.20 | 2.20 | 2.20 | 2.20 |
| Sodium saccharine | 0.20 | 0.20 | 0.20 | 0.20 | 0.20 | 0.20 |
| Sodium fluoride | 0.22 | 0.22 | 0.22 | 0.22 | 0.22 | 0.22 |
| Vitamin E | 0.20 | 0.20 | 0.20 | 0.20 | 0.20 | 0.20 |
| Sodium carboxy methyl cellulose | 0.60 | 0.50 | 0.50 | 0.40 | 1.50 | 2.50 |
| Xanthan gum |  |  |  | 0.20 |  |  |
| Sodium polyacrylic acid |  | 0.50 |  | 0.20 |  |  |
| Sodium alginate |  |  | 0.50 | 0.20 |  |  |
| Flavoring | 1.00 | 1.00 | 1.00 | 1.00 | 1.00 | 1.00 |
| Purified water | 30.68 | 30.18 | 30.18 | 30.18 | 39.68 | 28.68 |

Experimental Example 1-1

Viscosity of Prepared Toothpaste (Measurement of Viscosity Using Brookfield Viscometer)

For the toothpaste prepared as Examples 1 to 5 and Comparative example 1 of Table 1, in order to measure the viscosity at a room temperature (25□), the viscosity values were measured by rotating at a rotation speed of 20 rotations per minute using spindle No. 7 with Brookfield viscometer RVT type.

TABLE 2

|  | Example 1 | Example 2 | Example 3 | Example 4 | Example 5 | Comparative example 1 |
|---|---|---|---|---|---|---|
| Viscosity (1,000 cP) | 5.5 | 12 | 13 | 15 | 40 | 60 |

Comparative example 1 showed the high viscosity, but on the other hand, Examples 1 to 5 showed a viscosity in a range of 5,500 to 40,000 cP.

Experimental Example 1-2

Degree of Penetrating into Toothbrush Bristles

For the toothpaste prepared as Examples 1 to 5 and Comparative example 1 of Table 1, the toothpaste compositions in a gel phase of Examples 1 to 5 were put in pump-type containers, and the toothpaste composition in a paste phase of Comparative example 1 was put in a tube, and they were discharged to a toothbrush having a hole interval (interval between a toothbrush bristle and a bristle) of 1.5 mm, and the toothpaste safely arrived on the bristles, and in 10 seconds, the penetration depth at which the toothpaste extended from the top to the bottom of the toothbrush bristles was measured, and the result was as the following Table 3.

TABLE 3

|  | Example 1 | Example 2 | Example 3 | Example 4 | Example 5 | Comparative example 1 |
|---|---|---|---|---|---|---|
| Penetrating depth (mm) | 2 | 1 | 1 | 1 | 1 | No penetrating |

It could be seen that the paste toothpaste according to Comparative example 1 did not penetrate into the bristles, while Examples 1 to 5 penetrated into the bristles in a depth of 1-2 mm in the spaces among the bristles.

In addition, for the toothpaste prepared as Examples 1 to 5 and Comparative example 1 of Table 1, the toothpaste compositions in a gel phase of Examples 1 to 5 were put in pump-type containers, and the toothpaste composition in a paste phase of Comparative example 1 was put in a tube, and they were discharged to a toothbrush having a hole interval (interval between a toothbrush bristle and a bristle) of 2 mm, and the toothpaste safely arrived on the toothbrush bristles, and in 10 seconds, the penetration depth was measured, and the result was as the following Table 4.

TABLE 4

|  | Example 1 | Example 2 | Example 3 | Example 4 | Example 5 | Comparative example 1 |
|---|---|---|---|---|---|---|
| Penetrating depth (mm) | 4 | 3 | 2 | 5 | 1.5 | No penetrating |

It could be seen that the paste toothpaste according to Comparative example 1 did not penetrate into the bristles, while Examples 1 to 5 penetrated into the bristles in a depth of 1.5-5 mm in the spaces among the bristles.

As could be seen by the results of Table 3 and Table 4, as a toothbrush having a large hole interval was used, the difference in penetration into the toothbrush bristles between Comparative example and Examples were remarkably shown.

As could be seen by the results of Table 3 and Table 4, it could be seen that the toothpaste according to Examples 1-5 penetrated into the toothbrush bristles well when contained in a pump-type container and discharged to a toothbrush, and thus it had an effect of delivering a medicinal ingredient to the oral cavity continuously during brushing, compared to Comparative example 1.

II. PREPARATIVE EXAMPLE 2 OF PUMP-TYPE TOOTHPASTE COMPOSITION

The toothpaste compositions of Examples and Comparative examples were prepared with ingredients and composition ratios shown in the following Table 5. Powder ingredients such as purified water, liquid polyol, flavoring, a pharmaceutical agent, a surfactant, a binder, saccharine were completely dispersed to mix primarily, and then an abrasive such as silica and the like and a pharmaceutical agent were added and mixed in a vacuum to prepare toothpaste compositions.

TABLE 5

|  | Example 1 | Example 2 | Example 3 | Example 4 | Example 5 | Example 6 | Example 7 | Example 8 | Example 9 | Example 10 | Example 11 | Example 12 | Example 13 | Example 14 |
|---|---|---|---|---|---|---|---|---|---|---|---|---|---|---|
| Precipitated silica | 15 | 15 | 15 | 15 | 15 | 15 | 15 | 15 | 15 | 15 | 15 | 15 | 15 | 15 |
| Glycerin | 50 | 50 | 50 | 50 | 50 | 50 | 50 | 50 | 50 | 50 | 50 | 50 | 50 | 50 |
| Sodium lauryl sulfate | 2.2 | 2.2 | 2.2 | 2.2 | 2.2 | 2.2 | 2.2 | 2.2 | 2.2 | 2.2 | 2.2 | 2.2 | 2.2 | 2.2 |
| Sodium saccharine | 0.2 | 0.2 | 0.2 | 0.2 | 0.2 | 0.2 | 0.2 | 0.2 | 0.2 | 0.2 | 0.2 | 0.2 | 0.2 | 0.2 |
| Sodium fluoride | 0.22 | 0.22 | 0.22 | 0.22 | 0.22 | 0.22 | 0.22 | 0.22 | 0.22 | 0.22 | 0.22 | 0.22 | 0.22 | 0.22 |

TABLE 5-continued

|  | Example 1 | Example 2 | Example 3 | Example 4 | Example 5 | Example 6 | Example 7 | Example 8 | Example 9 | Example 10 | Example 11 | Example 12 | Example 13 | Example 14 |
|---|---|---|---|---|---|---|---|---|---|---|---|---|---|---|
| Vitamin E | 0.2 | 0.2 | 0.2 | 0.2 | 0.2 | 0.2 | 0.2 | 0.2 | 0.2 | 0.2 | 0.2 | 0.2 | 0.2 | 0.2 |
| PVM/MA | 1 | 1 | 0.1 | 0.5 | 2 |  |  |  |  |  |  |  |  |  |
| PVP |  |  |  |  |  | 1 | 1 | 0.1 | 0.5 | 2 |  |  |  |  |
| HPMC |  |  |  |  |  |  |  |  |  |  | 1 | 1 | 0.1 | 0.5 |
| HPC |  |  |  |  |  |  |  |  |  |  |  |  |  |  |
| Sodium carboxy methyl cellulose | 0.5 |  | 0.8 | 0.5 | 0.5 | 0.5 |  | 0.8 | 0.5 | 0.5 | 0.5 |  | 0.8 | 0.5 |
| Xanthan gum |  | 0.5 |  |  |  |  | 0.5 |  |  |  |  | 0.5 |  |  |
| Flavoring | 1 | 1 | 1 | 1 | 1 | 1 | 1 | 1 | 1 | 1 | 1 | 1 | 1 | 1 |
| Purified water | 29.68 | 29.68 | 30.28 | 30.18 | 28.68 | 29.68 | 29.68 | 30.28 | 30.18 | 28.68 | 29.68 | 29.68 | 30.28 | 30.18 |

|  | Example 15 | Example 16 | Example 17 | Example 18 | Example 19 | Example 20 | Example 21 | Example 22 | Example 23 | Example 24 | Comparative Example 1 | Comparative Example 2 | Comparative Example 3 | Comparative Example 4 |
|---|---|---|---|---|---|---|---|---|---|---|---|---|---|---|
| Precipitated silica | 15 | 15 | 15 | 15 | 15 | 15 | 15 | 15 | 15 | 15 | 15 | 15 | 15 | 15 |
| Glycerin | 50 | 50 | 50 | 50 | 50 | 50 | 50 | 50 | 50 | 50 | 50 | 50 | 50 | 50 |
| Sodium lauryl sulfate | 2.2 | 2.2 | 2.2 | 2.2 | 2.2 | 2.2 | 2.2 | 2.2 | 2.2 | 2.2 | 2.2 | 2.2 | 2.2 | 2.2 |
| Sodium saccharine | 0.2 | 0.2 | 0.2 | 0.2 | 0.2 | 0.2 | 0.2 | 0.2 | 0.2 | 0.2 | 0.2 | 0.2 | 0.2 | 0.2 |
| Sodium fluoride | 0.22 | 0.22 | 0.22 | 0.22 | 0.22 | 0.22 | 0.22 | 0.22 | 0.22 | 0.22 | 0.22 | 0.22 | 0.22 | 0.22 |
| Vitamin E | 0.2 | 0.2 | 0.2 | 0.2 | 0.2 | 0.2 | 0.2 | 0.2 | 0.2 | 0.2 | 0.2 | 0.2 | 0.2 | 0.2 |
| PVM/MA |  |  |  |  |  |  | 1 |  |  |  |  |  |  |  |
| PVP |  |  |  |  |  |  |  | 1 |  |  |  |  |  |  |
| HPMC | 2 |  |  |  |  |  |  |  | 1 |  |  |  |  |  |
| HPC |  | 1 | 1 | 0.1 | 0.5 | 2 |  |  |  | 1 |  |  |  |  |
| Sodium carboxy methyl cellulose | 0.5 | 0.5 |  | 0.8 | 0.5 | 0.5 |  |  |  |  |  | 1 | 0.5 |  |
| Xanthan gum |  |  | 0.5 |  |  |  |  |  |  |  | 1 | 0.5 |  | 3 |
| Flavoring | 1 | 1 | 1 | 1 | 1 | 1 |  |  |  |  | 1 | 1 | 1 | 1 |
| Purified water | 28.68 | 29.68 | 29.68 | 30.28 | 30.18 | 28.68 | 31.18 | 31.18 | 31.18 | 31.18 | 30.18 | 30.18 | 30.18 | 28.18 |

Experimental Example 2-1

Viscosity of Prepared Toothpaste (Measurement of Viscosity Using Brookfield Viscometer)

For the toothpaste prepared as Examples 1 to 24 and Comparative examples 1 to 4 of Table 5, in order to measure the viscosity at a room temperature (25□), the viscosity values were measured by rotating at a rotation speed of 20 rotations per minute using spindle No. 7 with Brookfield viscometer RVT type, and the result was as the following Table 6.

TABLE 6

|  | Example 1 | Example 2 | Example 3 | Example 4 | Example 5 | Example 6 | Example 7 | Example 8 | Example 9 | Example 10 | Example 11 | Example 12 | Example 13 | Example 14 |
|---|---|---|---|---|---|---|---|---|---|---|---|---|---|---|
| Viscosity (1,000 cP) | 20 | 15 | 15 | 12 | 28 | 16 | 11 | 11 | 8 | 24 | 17 | 12 | 12 | 9 |

TABLE 6-continued

| | Example 15 | Example 16 | Example 17 | Example 18 | Example 19 | Example 20 | Example 21 | Example 22 | Example 23 | Example 24 | Comparative Example 1 | Comparative Example 2 | Comparative Example 3 | Comparative Example 4 |
|---|---|---|---|---|---|---|---|---|---|---|---|---|---|---|
| Viscosity (1,000 cP) | 25 | 23 | 18 | 18 | 15 | 30 | 10 | 5 | 6 | 12 | 20 | 18 | 15 | 50 |

Comparative examples 1 to 4 and Examples 1 to 24 showed the viscosity in a range of 40,000 cP or less all.

Experimental Example 2-2

Degree of Penetrating into Toothbrush Bristles

The toothpaste prepared as Examples 1 to 24 and Comparative examples 1 to 4 of Table 5 were put in pump-type containers, and they were discharged to a toothbrush having a hole interval (interval between a toothbrush bristle and a bristle) of 1-1.5 mm, and the toothpaste safely arrived on the toothbrush bristle, and in 10 seconds, the penetration depth at which the toothpaste extended from the top to the bottom of thetoothbrush bristle was measured, and the result was as the following Table 7.

TABLE 7

| | Example 1 | Example 2 | Example 3 | Example 4 | Example 5 | Example 6 | Example 7 | Example 8 | Example 9 | Example 10 | Example 11 | Example 12 | Example 13 | Example 14 |
|---|---|---|---|---|---|---|---|---|---|---|---|---|---|---|
| Penetrating depth (mm) | 4 | 4 | 4 | 4 | 1.5 | 4.5 | 4.5 | 4.5 | 4.5 | 2 | 2.5 | 3.5 | 3.5 | 4.5 |

| | Example 15 | Example 16 | Example 17 | Example 18 | Example 19 | Example 20 | Example 21 | Example 22 | Example 23 | Example 24 | Comparative Example 1 | Comparative Example 2 | Comparative Example 3 | Comparative Example 4 |
|---|---|---|---|---|---|---|---|---|---|---|---|---|---|---|
| Penetrating depth (mm) | 2 | 2 | 2.5 | 2.5 | 3 | 1.5 | 4.5 | 5 | 5 | 3.5 | 1 | 1 | 1 | No penetrating |

The paste toothpaste according to Comparative examples 1-4 showed an appropriate viscosity, but the penetrating depth was significantly decreased, compared to Examples 1 to 24. Through this, it was expected that Comparative examples 1 to 4 had a high elastic modulus.

Experimental Example 2-3

Tan δ (Loss Modulus (G')/Elastic Modulus (G"))

The amplitude sweep oscillation test was conducted using Paar Physica rheology measuring instrument, and the elastic modulus and viscosity coefficient were read when the shear stress was 1, and Tan δ values for them were obtained.

TABLE 8

| | Example 1 | Example 2 | Example 3 | Example 4 | Example 5 | Example 6 | Example 7 | Example 8 | Example 9 | Example 10 | Example 11 | Example 12 | Example 13 | Example 14 |
|---|---|---|---|---|---|---|---|---|---|---|---|---|---|---|
| Tan δ | 0.5 | 0.5 | 0.5 | 0.5 | 0.8 | 0.55 | 0.55 | 0.55 | 0.55 | 0.85 | 0.4 | 0.45 | 0.45 | 0.55 |

TABLE 8-continued

|  | Example 15 | Example 16 | Example 17 | Example 18 | Example 19 | Example 20 | Example 21 | Example 22 | Example 23 | Example 24 | Comparative Example 1 | Comparative Example 2 | Comparative Example 3 | Comparative Example 4 |
|---|---|---|---|---|---|---|---|---|---|---|---|---|---|---|
| Tan δ | 0.85 | 0.75 | 0.75 | 0.75 | 0.45 | 0.65 | 0.55 | 0.9 | 0.9 | 0.65 | 0.25 | 0.35 | 0.3 | 0.01 |

Although the larger the value of Tan δ, the higher the viscosity of the toothpaste by using a polymer having a high viscosity coefficient, it means that a structure with flowability can be produced. According to the Table 8, it can be seen that Examples have higher values of Tan δ, compared to Comparative examples.

Experimental Example 2-4

Measurement of Rich Feeling

After using the toothpaste according to Examples 7 and 8 and Comparative example 1 for the evaluation group, the evaluation questionnaire was progressed about the attribute that was the evaluation scale of rich feeling during brushing. The questionnaire was progressed on a 5-point scale, and it was evaluated as 1-point was low in texture and 5-point was high. As a result, as shown in the FIG., it was confirmed that the bubble texture and satisfaction of bubbles in case of using Examples were higher than Comparative example.

III. PREPARATIVE EXAMPLE 3 OF PUMP-TYPE TOOTHPASTE COMPOSITION

The toothpaste compositions of Examples and Comparative examples were prepared with ingredients and composition ratios shown in the following Table 9. Purified water, liquid polyol, flavoring, a pharmaceutical agent, xanthan gum, saccharine, a preservative, and powder ingredients such as a surfactant were completely dispersed to mix primarily, and then an abrasive such as silica and the like and a pharmaceutical agent were added and mixed in a vacuum to prepare toothpaste compositions.

TABLE 9

|  | Example 1 | Example 2 | Example 3 | Example 4 | Example 5 | Example 6 | Comparative example 1 | Comparative example 2 | Comparative example 3 |
|---|---|---|---|---|---|---|---|---|---|
| Precipitated silica | 10.00 | 20.00 | 30.00 | 40.00 |  |  | 10.00 | 20.00 | 30.00 |
| Calcium carbonate |  |  |  |  | 20.00 |  |  |  |  |
| Calcium hydrogen phosphate |  |  |  |  |  | 20.00 |  |  |  |
| Glycerin | 80.00 | 70.00 | 60.00 | 50.00 | 70.00 | 70.00 | 45.00 | 45.00 | 45.00 |
| Sodium lauryl sulfate | 2.00 | 2.00 | 2.00 | 2.00 | 2.00 | 2.00 | 2.00 | 2.00 | 2.00 |
| Sodium saccharine | 0.20 | 0.20 | 0.20 | 0.20 | 0.20 | 0.20 | 0.20 | 0.20 | 0.20 |
| Xanthan gum | 1.00 | 1.00 | 1.00 | 1.00 | 1.00 | 1.00 | 1.00 | 1.00 | 1.00 |
| Sodium fluoride | 0.22 | 0.22 | 0.22 | 0.22 | 0.22 | 0.22 | 0.22 | 0.22 | 0.22 |
| Vitamin E | 0.20 | 0.20 | 0.20 | 0.20 | 0.20 | 0.20 | 0.20 | 0.20 | 0.20 |
| Flavoring | 1.00 | 1.00 | 1.00 | 1.00 | 1.00 | 1.00 | 1.00 | 1.00 | 1.00 |
| Purified water | 5.38 | 5.38 | 5.38 | 5.38 | 5.38 | 5.38 | 40.38 | 30.38 | 20.38 |

Experimental Example 3-1

Time to Harden After Discharging Pump-Type Toothpaste

The toothpaste compositions prepared as Examples and Comparative examples of Table 9 were filled to a 24 well plate, and then were dried in a dry oven equipped with a fan at 60□ for 48 hours. Then, the degree of hardening when applying pressure to the toothpaste using a probe-rod (round-shaped pen) was determined to evaluate the degree of hardening of the toothpaste.

For the degree of hardening, it was marked as 'hardened' when contents were hardened to the extent that they were not scratched, and it was marked as 'not hardened' when contents were scratched or the probe-rod was inserted into the contents. The result was described in Table 10.

TABLE 10

|  | Example 1 | Example 2 | Example 3 | Example 4 | Example 5 | Example 6 | Comparative example 1 | Comparative example 2 | Comparative example 3 |
| --- | --- | --- | --- | --- | --- | --- | --- | --- | --- |
| Degree of hardening | Not hardened | Not hardened | Not hardened | Not hardened | Not hardened | Not hardened | Hardened | Hardened | Hardened |

As could be seen from the result, Comparative examples 1 to 3 were shown as 'hardened' all, while Examples 1 to 6 were shown as 'not hardened'.

Experimental Example 3-2

Compression Strength TEST

The toothpaste compositions prepared as Examples and Comparative examples of Table 9 were filled in a 24 well plate and were dried at 60□ for 48 hours, and then the compression strength of the toothpaste was measured with a 0.4~2 cm probe, using a texture analyzer. It was confirmed that one showing 5 g or less in the measurement was not hardened, and it was confirmed that the compression strength increased due to hardening of the surface in case of receiving a force of 5 g or more. The result was described in Table 11.

TABLE 11

|  | Example 1 | Example 2 | Example 3 | Example 4 | Example 5 | Example 6 | Comparative example 1 | Comparative example 2 | Comparative example 3 |
| --- | --- | --- | --- | --- | --- | --- | --- | --- | --- |
| Compression strength | 5 g or less | 5 g or less | 5 g or less | 5 g or less | 5 g or less | 5 g or less | 9 g | 15 g | 50 g |

As could be seen from the result, Examples 1 to 6 showed the compression strength of '5 g or less' all, while Comparative examples 1 to 3 showed the compression strength of 5 g or more and therefore it was shown that their surfaces were hardened.

Experimental Example 3-3

Test for Observing Hardening of Pump Inlet

The toothpaste compositions prepared as Examples and Comparative examples of Table 9 were put in a pump-type container, and after the contents of this pump-type toothpaste was discharged, the pump was dried at 60□ for 6 hours. Then, the pump pressure was measured using a texture analyzer. The result was described in Table 12.

TABLE 12

| | Example 1 | Example 2 | Example 3 | Example 4 | Example 5 | Example 6 | Example 7 | Comparative example 1 | Comparative example 2 | Comparative example 3 |
|---|---|---|---|---|---|---|---|---|---|---|
| Compression strength | 2.6 kg | 2.6 kg | 2.6 kg | 2.6 kg | 2.6 kg | 2.6 kg | 2.6 kg | 3.2 kg | 3.7 kg | Impossible to discharge |

As a result, Examples 1 to 6 showed the discharge pressure of 3 kg or less all, while Comparative examples 1 to 3 showed the discharge pressure of 3 kg or more, and therefore it could be seen that their inlets were hardened and thereby the discharge pressure increased.

IV. PREPARATIVE EXAMPLE 4 OF PUMP-TYPE TOOTHPASTE COMPOSITION

The toothpaste compositions of Examples and Comparative examples were prepared with ingredients and composition ratios shown in the following Table 13. Purified water, liquid polyol, flavoring, a pharmaceutical agent, xanthan gum, saccharine, a preservative, powder ingredients such as a surfactant (HCO40, HLB 12.5; TWEEN 60, HLB 14.9; and SPAN 80, HLB 4.3) were completely dispersed to mix primarily, and then an abrasive such as silica and the like and a pharmaceutical agent were added and mixed in a vacuum to prepare toothpaste compositions.

Experimental Example 4-1

Phase Stability

Comparative example 2 comprising an excessive amount of surfactant did not maintain the phase of toothpaste and was modified. Thus, the evaluation itself was impossible in subsequent experiments.

Experimental Example 4-2

Time to Harden After Discharging Pump-Type Toothpaste

The toothpaste compositions prepared as Examples and Comparative examples of Table 13 were filled to a 24 well plate, and then were dried in a dry oven equipped with a fan at 60□ for 48 hours. Then, the degree of hardening when applying pressure to the toothpaste using a probe-rod (round-shaped pen) was determined to evaluate the degree of hardening of the toothpaste.

For the degree of hardening, it was marked as 'hardened' when contents were hardened to the extent that they were not scratched, and it was marked as 'not hardened' when contents were scratched or the probe-rod was inserted into the contents. The result was described in Table 14.

TABLE 13

| | Example 1 | Example 2 | Example 3 | Example 4 | Example 5 | Example 6 | Example 7 | Example 8 | Example 9 | Example 10 | Example 11 | Example 12 | Comparative example 1 | Comparative example 2 |
|---|---|---|---|---|---|---|---|---|---|---|---|---|---|---|
| Precipitated silica | 15 | 15 | 15 | 15 | 15 | 15 | 15 | 15 | 15 | 15 | 15 | 15 | 15 | 15 |
| Glycerin | 40 | 40 | 40 | 40 | 40 | 40 | 40 | 40 | 40 | 40 | 40 | 40 | 40 | 40 |
| Sodium lauryl sulfate | 2.2 | 2.2 | 2.2 | 2.2 | 2.2 | 2.2 | 2.2 | 2.2 | 2.2 | 2.2 | 2.2 | 2.2 | 2.2 | 2.2 |
| Sodium saccharine | 0.2 | 0.2 | 0.2 | 0.2 | 0.2 | 0.2 | 0.2 | 0.2 | 0.2 | 0.2 | 0.2 | 0.2 | 0.2 | 0.2 |
| Xanthan gum | 1 | 1 | 1 | 1 | 1 | 1 | 1 | 1 | 1 | 1 | 1 | 1 | 1 | 1 |
| Sodium fluoride | 0.22 | 0.22 | 0.22 | 0.22 | 0.22 | 0.22 | 0.22 | 0.22 | 0.22 | 0.22 | 0.22 | 0.22 | 0.22 | 0.22 |
| Vitamin E | 0.2 | 0.2 | 0.2 | 0.2 | 0.2 | 0.2 | 0.2 | 0.2 | 0.2 | 0.2 | 0.2 | 0.2 | 0.2 | 0.2 |
| HCO 40 | 0.05 | 0.2 | 0.5 | 1 | 5 | 10 | | | 0.5 | | 0.1 | 0.5 | | 20 |
| TWEEN 60 | | | | | | | 1 | | 0.5 | 0.5 | 0.1 | 0.5 | | |
| SPAN 80 | | | | | | | | 1 | | 0.5 | 0.1 | 0.5 | | |
| Flavoring | 1 | 1 | 1 | 1 | 1 | 1 | 1 | 1 | 1 | 1 | 1 | 1 | 1 | 1 |
| Purified water | 40.13 | 39.98 | 39.68 | 39.18 | 35.18 | 30.18 | 39.18 | 39.18 | 39.18 | 39.18 | 39.88 | 38.68 | 40.18 | 20.18 |

TABLE 14

| | Example 1 | Example 2 | Example 3 | Example 4 | Example 5 | Example 6 | Example 7 | Example 8 |
|---|---|---|---|---|---|---|---|---|
| Evaluation result | Not hardened | Not hardened | Not hardened | Not hardened | Not hardened | Not hardened | Not hardened | Not hardened |

| | Example 9 | Example 10 | Example 11 | Example 12 | Comparative example 1 | Comparative example 2 |
|---|---|---|---|---|---|---|
| Evaluation result | Not hardened | Not hardened | Not hardened | Not hardened | Hardened | Not measurable |

As could be seen from the result, Comparative example 1 was shown as 'hardened', while Examples 1 to 12 were shown as 'not hardened'.

Experimental Example 4-3

Compression Strength TEST

The toothpaste compositions prepared as Examples and Comparative examples of Table 13 were filled in a 24 well plate and were dried at 60□ for 48 hours, and then the compression strength of the toothpaste was measured with a 0.4~2 cm probe, using a texture analyzer. It was confirmed that one showing 5 g or less in the measurement was not hardened, and it was confirmed that the compression strength increased due to hardening of the surface in case of receiving a force of 5 g or more. The result was described in Table 15.

TABLE 15

| | Example 1 | Example 2 | Example 3 | Example 4 | Example 5 | Example 6 | Example 7 | Example 8 | Example 9 | Example 10 | Example 11 | Example 12 | Comparative example 1 | Comparative example 2 |
|---|---|---|---|---|---|---|---|---|---|---|---|---|---|---|
| Evaluation result | 5 g or less | 5 g or less | 5 g or less | 5 g or less | 5 g or less | 5 g or less | 5 g or less | 5 g or less | 5 g or less | 5 g or less | 5 g or less | 5 g or less | 7 g | Not measurable |

As could be seen from the result, Examples 1 to 12 showed the compression strength of '5 g or less' all, while Comparative example 1 showed the compression strength of 5 g or more and therefore it was shown that its surface was hardened.

Experimental Example 4-4

Test for Observing Hardening of Pump Inlet

The toothpaste compositions prepared as Examples and Comparative examples of Table 13 were put in a pump-type container, and after the contents of this pump-type toothpaste was discharged, the pump was dried at 60□ for 6 hours. Then, the pump pressure was measured using a texture analyzer. The result was described in Table 16.

TABLE 16

| | Example 1 | Example 2 | Example 3 | Example 4 | Example 5 | Example 6 | Example 7 | Example 8 | Example 9 | Example 10 | Example 11 | Example 12 | Comparative example 1 | Comparative example 2 |
|---|---|---|---|---|---|---|---|---|---|---|---|---|---|---|
| Evaluation result | 2.9 kg | 2.8 kg | 2.7 kg | 2.6 kg | 2.5 kg | 2.4 kg | 2.5 kg | 2.5 kg | 2.5 kg | 2.5 kg | 2.6 kg | 2.5 kg | 3.2 kg | Not meaurable |

As a result, Examples 1 to 12 showed the discharge pressure of 3 kg or less all, while Comparative example 1 showed the discharge pressure of 3 kg or more, and therefore it could be seen that its inlet was hardened and thereby the discharge pressure increased.

V. PREPARATIVE EXAMPLE 5 OF PUMP-TYPE TOOTHPASTE COMPOSITION

The toothpaste compositions of Examples and Comparative examples were prepared with ingredients and composition ratios shown in the following Table 17. Purified water, liquid polyol, flavoring, a pharmaceutical agent, xanthan gum, saccharine, a preservative, powder ingredients such as a surfactant were completely dispersed to mix primarily, and then an abrasive such as silica and the like and a pharmaceutical agent were added and mixed in a vacuum to prepare toothpaste compositions.

TABLE 17

|  | Example 1 | Example 2 | Example 3 | Example 4 | Example 5 | Example 6 | Example 7 | Comparative example 1 | Comparative example 2 | Comparative example 3 |
|---|---|---|---|---|---|---|---|---|---|---|
| Precipitated silica | 15.00 | 15.00 | 15.00 | 15.00 | 15.00 | 15.00 | 15.00 | 15.00 | 15.00 | 15.00 |
| Glycerin | 45.00 | 45.00 | 45.00 | 45.00 | 45.00 | 45.00 | 45.00 | 45.00 | 45.00 | 45.00 |
| Sodium lauryl sulfate | 1.00 | 1.00 | 2.00 | 2.00 | 2.00 | 2.00 | 2.00 |  | 2.00 |  |
| Organic oil | 0.50 | 1.00 | 1.00 | 2.00 | 5.00 | 10.00 | 20.00 |  |  | 30.00 |
| Sodium saccharine | 0.20 | 0.20 | 0.20 | 0.20 | 0.20 | 0.20 | 0.20 | 0.20 | 0.20 | 0.20 |
| Xanthan gum | 1.00 | 1.00 | 1.00 | 1.00 | 1.00 | 1.00 | 1.00 | 1.00 | 1.00 | 1.00 |
| Sodium fluoride | 0.22 | 0.22 | 0.22 | 0.22 | 0.22 | 0.22 | 0.22 | 0.22 | 0.22 | 0.22 |
| Vitamin E | 0.20 | 0.20 | 0.20 | 0.20 | 0.20 | 0.20 | 0.20 | 0.20 | 0.20 | 0.20 |
| Flavoring | 0.50 | 0.50 | 0.50 | 0.50 | 0.50 | 0.50 | 0.50 | 0.50 | 0.50 | 0.50 |
| Purified water | 36.38 | 35.88 | 34.88 | 33.88 | 31.10 | 26.10 | 15.83 | 37.88 | 35.88 | 7.88 |

Experimental Example 5-1

Phase Stability

Comparative example 3 comprising an excessive amount of oil only without a surfactant had a problem in stability. Thus, the evaluation itself was impossible in subsequent experiments.

Experimental Example 5-2

Time to Harden After Discharging Pump-Type Toothpaste

The toothpaste compositions prepared as Examples and Comparative examples of Table 17 were filled to a 24 well plate, and then were dried in a dry oven equipped with a fan at 60□ for 48 hours. Then, the degree of hardening when applying pressure to the toothpaste using a probe-rod (round-shaped pen) was determined to evaluate the degree of hardening of the toothpaste.

For the degree of hardening, it was marked as 'hardened' when contents were hardened to the extent that they were not scratched, and it was marked as 'not hardened' when contents were scratched or the probe-rod was inserted into the contents. The result was described in Table 18.

TABLE 18

|  | Example 1 | Example 2 | Example 3 | Example 4 | Example 5 | Example 6 | Example 7 | Comparative example 1 | Comparative example 2 | Comparative example 3 |
|---|---|---|---|---|---|---|---|---|---|---|
| Degree of hardening | Not hardened | Not hardened | Not hardened | Not hardened | Not hardened | Not hardened | Not hardened | Hardened | Hardened | Not hardened |

As could be seen from the result, Comparative examples 1 and 2 were shown as 'hardened', while Examples 1 to 7 were shown as 'not hardened'.

Experimental Example 5-3

Compression Strength TEST

The toothpaste compositions prepared as Examples and Comparative examples of Table 17 were filled in a 24 well plate and were dried at 60□ for 48 hours, and then the compression strength of the toothpaste was measured with a 0.4~2 cm probe, using a texture analyzer. It was confirmed that one showing 5 g or less in the measurement was not hardened, and it was confirmed that the compression strength increased due to hardening of the surface in case of receiving a force of 5 g or more. The result was described in Table 19.

TABLE 19

| | Example 1 | Example 2 | Example 3 | Example 4 | Example 5 | Example 6 | Example 7 | Comparative example 1 | Comparative example 2 | Comparative example 3 |
|---|---|---|---|---|---|---|---|---|---|---|
| Compression strength | 5 g or less | 5 g or less | 5 g or less | 5 g or less | 5 g or less | 5 g or less | 5 g or less | 9 g | 7 g | Not measurable (Liquid separation) |

As could be seen from the result, Examples 1 to 7 showed the compression strength of '5 g or less' all, while Comparative examples 1 and 2 showed the compression strength of 5 g or more and therefore it was shown that their surfaces were hardened.

Experimental Example 5-4

Test for Observing Hardening of Pump Inlet

The toothpaste compositions prepared as Examples and Comparative examples of Table 17 were put in a pump-type container, and after the contents of this pump-type toothpaste was discharged, the pump was dried at 60□ for 6 hours. Then, the pump pressure was measured using a texture analyzer. The result was described in Table 20.

TABLE 20

| | Example 1 | Example 2 | Example 3 | Example 4 | Example 5 | Example 6 | Example 7 | Comparative example 1 | Comparative example 2 | Comparative example 3 |
|---|---|---|---|---|---|---|---|---|---|---|
| Compression strength | 2.9 kg | 2.8 kg | 2.6 kg | 2.6 kg | 2.6 kg | 2.6 kg | 2.6 kg | 3.2 kg | 3.3 kg | Not measurable (Liquid separation) |

As a result, it could be seen that all Examples 1 to 7 showed the discharge pressure of 3 kg or less, while Comparative examples 1 and 2 showed the discharge pressure of 3 kg or more, and therefore the inlet was hardened and thereby the discharge pressure increased.

The invention claimed is:

1. A pump-type toothpaste composition contained in a pump-type container, comprising:
   a non-ionic surfactant having an HLB value of 16 or less, and
   a solid abrasive selected from the group consisting of precipitated silica, calcium carbonate, calcium hydrogen phosphate and a mixture thereof;
   wherein the pump-type container is equipped with a piston inside thereof,
   wherein a content of the solid abrasive is 40% by weight or less based on a total weight of the composition, and
   a viscosity of the pump-type toothpaste composition is from 5,000 cP to 40,000 cP.

2. The pump-type toothpaste composition according to claim 1, wherein the non-ionic surfactant having an HLB value of 16 or less is one or more selected from the group consisting of glyceryl monostearate, polyoxyethylene monooleate, polyoxyethylene monostearate, potassium oleate, sodium oleate, sorbitan monolaurate, sorbitan monopalmitate, sorbitan monostearate, sorbitan tristearate, sorbitan monooleate, sorbitan trioleate, triethanolamine oleate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, and mixtures thereof.

3. The pump-type toothpaste composition according to claim 1, wherein the content of the non-ionic surfactant having an HLB value of 16 or less is 0.1 to 10% by weight based on the total weight of the composition.

4. The pump-type toothpaste composition according to claim 1, wherein the composition is in a suspended state in which a hydrophobic array is formed.

5. The pump-type toothpaste composition according to claim 1, wherein the pump of the pump-type container is a dip pump.

6. The pump-type toothpaste composition according to claim 1, wherein the toothpaste composition exhibits the compression strength of 5g or less, when the compression strength is measured with a 0.4 to 2 cm probe after drying the toothpaste composition at 60° C. for 5 hours using a texture analyzer.

7. A pump-type toothpaste comprising the pump-type toothpaste composition according to claim 1, and a pump-type container in which the pump-type toothpaste composition is contained.

8. The pump-type toothpaste according to claim 7, wherein the pump-type toothpaste exhibits the discharge pressure of 3 kg or less, when the pump pressure is measured using a texture analyzer, after discharging toothpaste and then drying it at 60° C. for 6 hours, for the pump-type toothpaste.

9. The pump-type toothpaste composition according to claim 1, wherein the composition is in a gel form.

* * * * *